(12) United States Patent
Smith et al.

(10) Patent No.: US 9,272,097 B2
(45) Date of Patent: *Mar. 1, 2016

(54) RETRACTABLE SAFETY SYRINGE WITH NON-LOADED SEAL

(71) Applicant: Credence Medsystems, Inc., Menlo Park, CA (US)

(72) Inventors: Jeffrey Smith, Irvine, CA (US); Daniel Thayer, Mission Viejo, CA (US); Rex O. Bare, Mission Viejo, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/010,181

(22) Filed: Aug. 26, 2013

(65) Prior Publication Data

US 2014/0052098 A1 Feb. 20, 2014

Related U.S. Application Data

(63) Continuation of application No. 12/842,884, filed on Jul. 23, 2010, now Pat. No. 8,517,986.

(51) Int. Cl.
*A61M 5/00* (2006.01)
*A61M 5/32* (2006.01)

(52) U.S. Cl.
CPC ............ *A61M 5/3221* (2013.01); *A61M 5/322* (2013.01); *A61M 5/3234* (2013.01); *A61M 2005/3235* (2013.01)

(58) Field of Classification Search
CPC .................. A61M 5/3221; A61M 2005/3235; A61M 5/322; A61M 5/3234
See application file for complete search history.

(56) References Cited

U.S. PATENT DOCUMENTS

| 6,193,695 B1 | 2/2001 | Rippstein |
| 6,458,105 B1 | 10/2002 | Rippstein |
| 7,572,247 B2 | 8/2009 | Smith et al. |
| 8,012,131 B2 | 9/2011 | Moser et al. |
| 8,517,986 B2 | 8/2013 | Smith et al. |

(Continued)

FOREIGN PATENT DOCUMENTS

WO 03/072181 9/2003

OTHER PUBLICATIONS

European Search Report mailed on Nov. 29, 2013 for European Application No. 11810503.

(Continued)

*Primary Examiner* — Rebecca E Eisenberg
(74) *Attorney, Agent, or Firm* — K&L Gates, LLP; Louis Cullman; Andrew L. Reibman

(57) ABSTRACT

A retractable safety syringe may have a needle, a syringe body, a shaft seal, and a plunger assembly. A proximal portion of the body and a piston of the plunger may define a vacuum chamber. The plunger assembly may comprise a shaft coupled to a piston. The shaft may have at least one non-engaging portion and at least one engaging portion. The plunger assembly is movable between a storage position and working positions. In the storage position, little or no force is exerted on the shaft seal by the non-engaging portion. In the working positions, the engaging portion is in sealing engagement with the shaft seal to seal the vacuum chamber. Stopper movement of the retractable safety syringe may be reduced or eliminated if the retractable safety syringe is prefilled.

19 Claims, 11 Drawing Sheets

(56) References Cited

U.S. PATENT DOCUMENTS

2003/0187388 A1 10/2003 Sharon et al.
2006/0253074 A1 11/2006 Thayer
2006/0264840 A1 11/2006 Thayer
2007/0000556 A1 1/2007 Smith et al.
2007/0250002 A1 10/2007 Oliver
2007/0250003 A1 10/2007 Bare et al.
2007/0255212 A1 11/2007 Smith et al.
2007/0260180 A1 11/2007 Smith et al.
2007/0260181 A1 11/2007 Smith et al.
2008/0027381 A1 1/2008 Smith et al.

OTHER PUBLICATIONS

International Search Report mailed on Dec. 6, 2011 for International Application No. PCT/US2011/045116 filed on Jul. 22, 2011.
Kinney, Stopper movement, gas bubbles in shipping and improving the container closure integrity of a pre-filled syringe. Power Point Presentation. Hyaluron Contact Manufacturing.
Zurkirch, Sustainability in pharmaceutical packaging made measurable. Power point Presentation. Dividella, Pharma Packaging Technology, Jun. 2009.

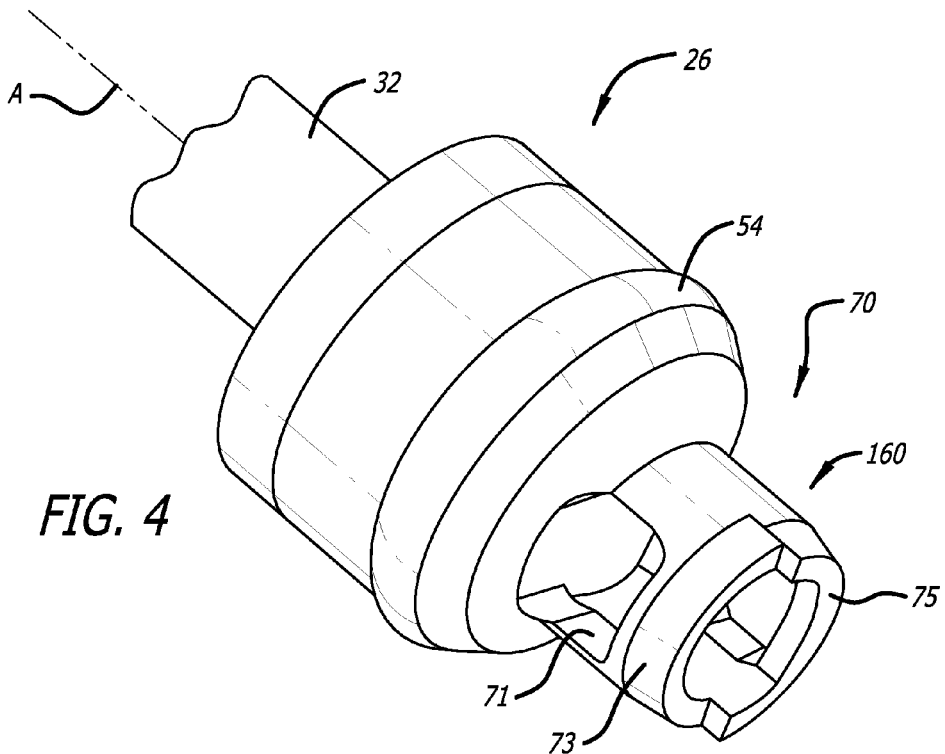
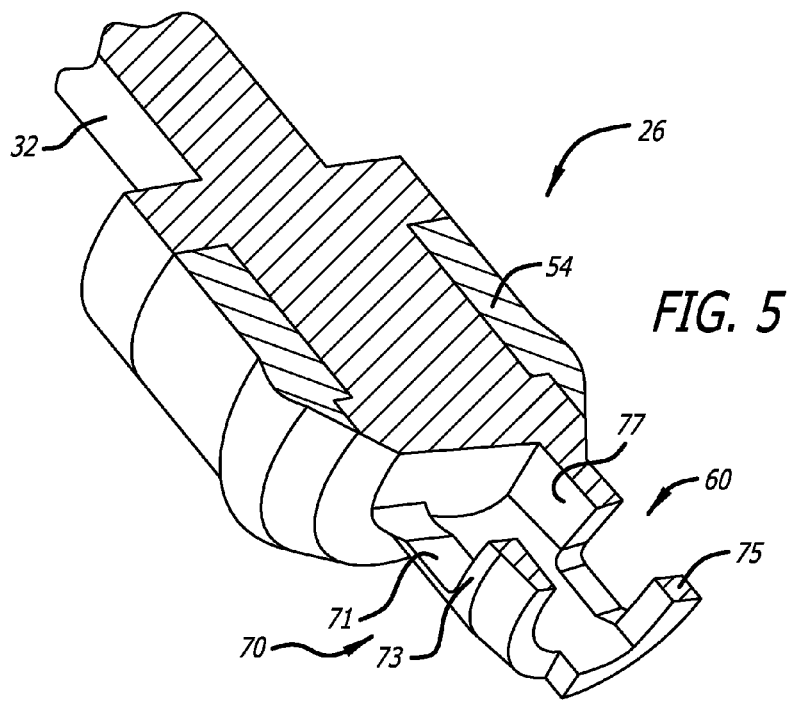

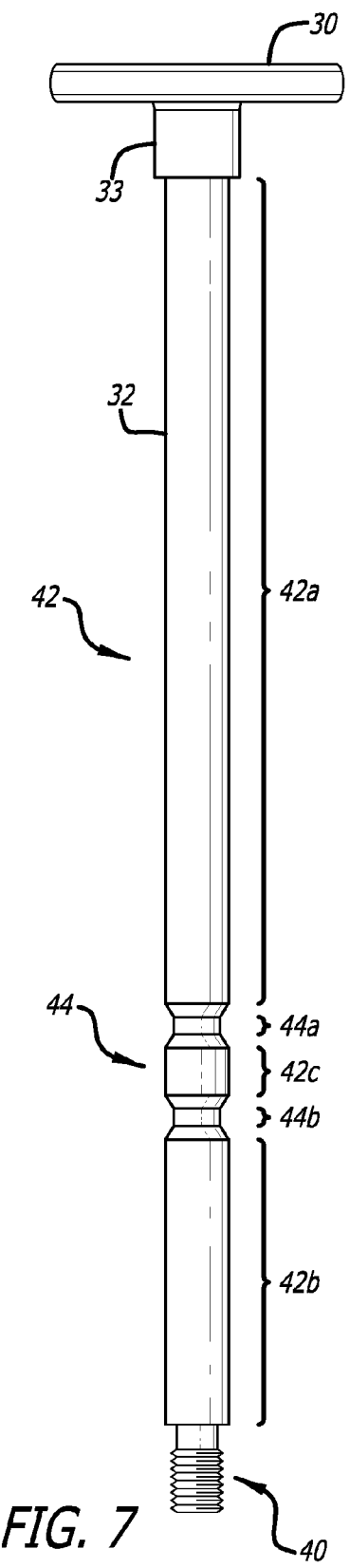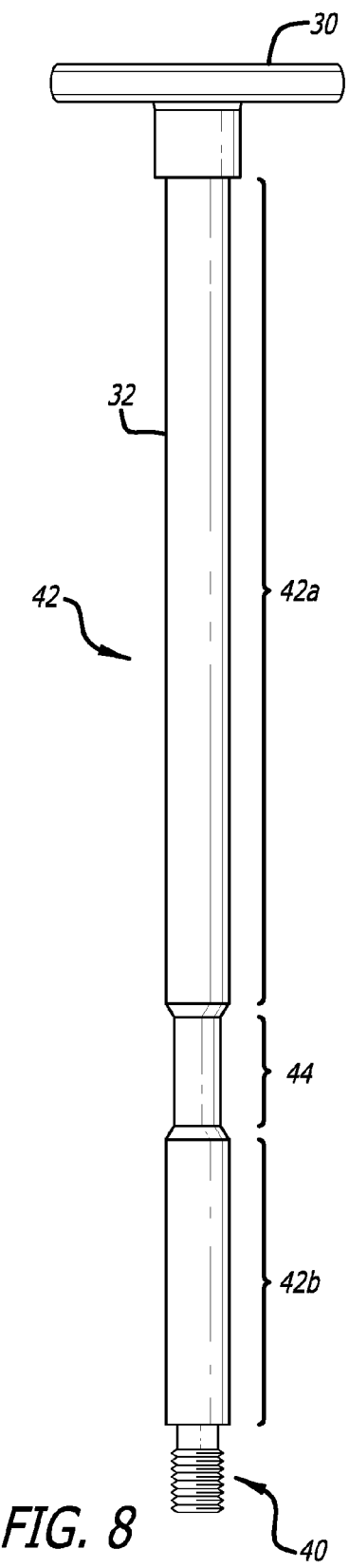
FIG. 7
FIG. 8

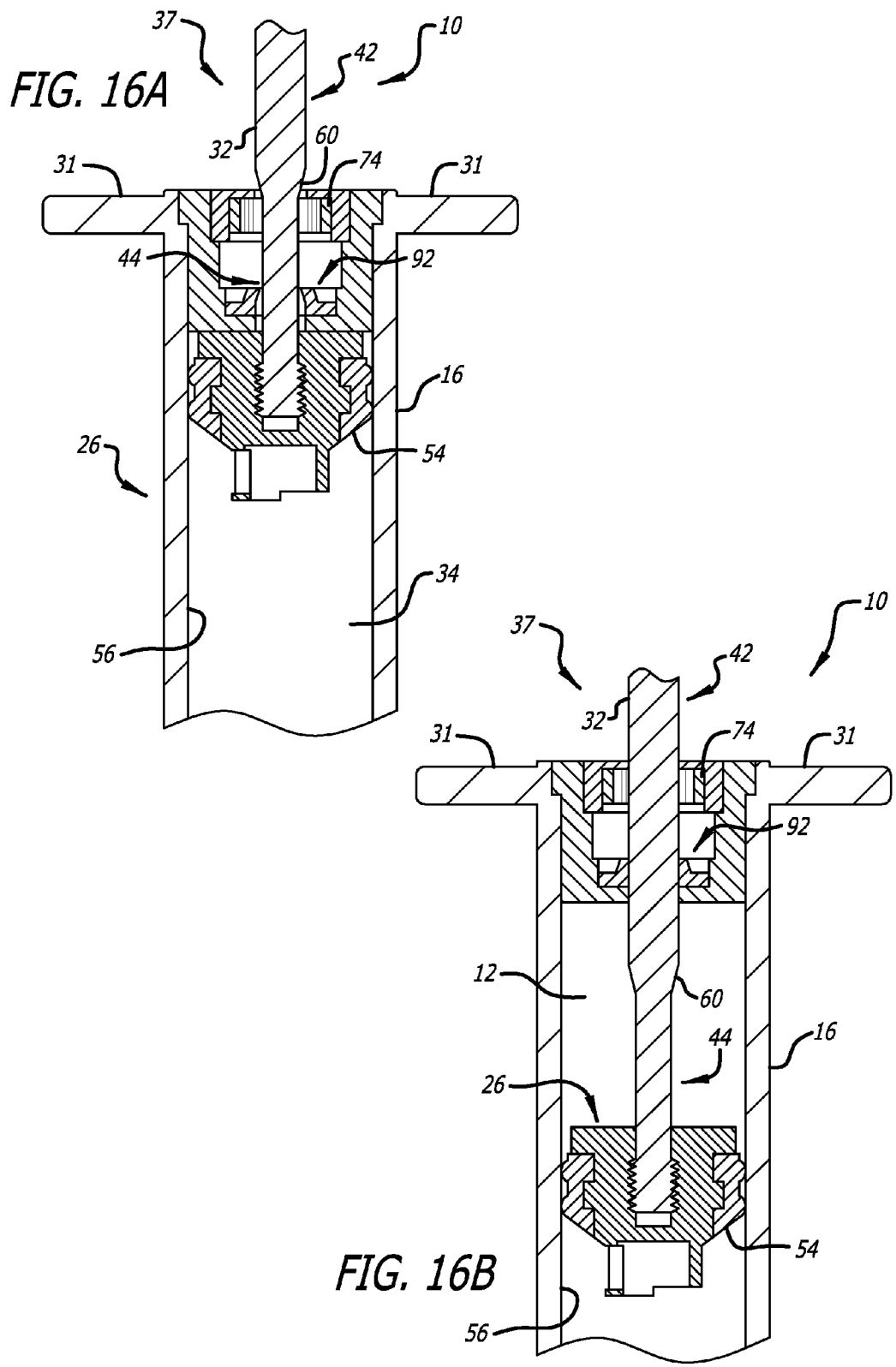

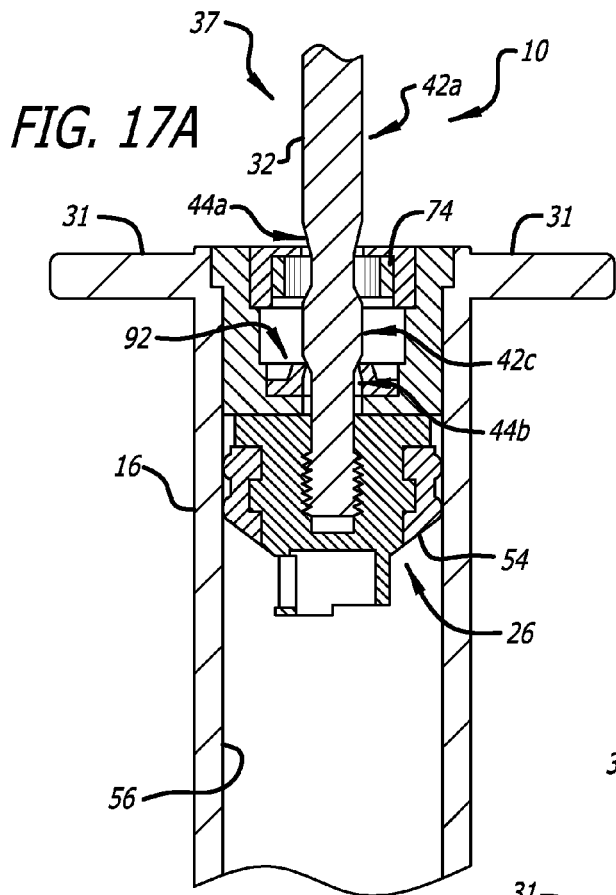
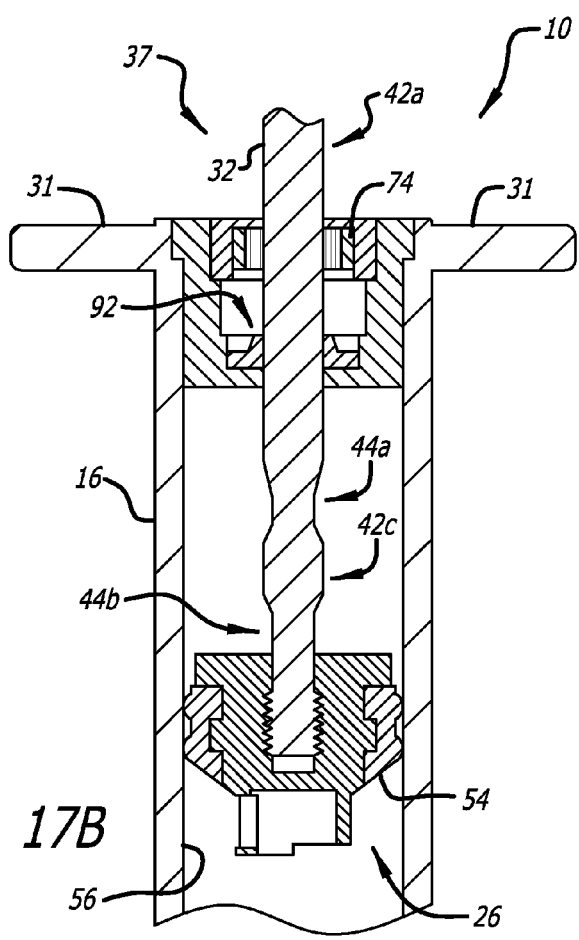

RETRACTABLE SAFETY SYRINGE WITH NON-LOADED SEAL

PRIORITY

This application claims priority to and the benefit as a continuation application of U.S. patent application Ser. No. 12/842,884, filed Jul. 23, 2010, entitled, "Retractable Safety Syringe with Non-Loaded Seal", the entire contents of which are incorporated herein by reference and relied upon.

BACKGROUND

In recent years, the public (e.g., medical personnel and healthcare providers, drug addicts, drug users, and the like) has become increasingly aware of the health hazards associated with needle reuse and accidental needle prickings. For example, at least twenty blood-borne pathogens may be transmitted by the reuse of needles or accidental needle prickings. For example, these blood borne pathogens may include and are not limited to Human Immunodeficiency Virus (HIV), Acquired Immunodeficiency Syndrome (AIDS), Hepatitis B, Hepatitis C, syphilis, malaria, tuberculosis, and herpes. Despite the awareness of the risk of needle reuse and accidental needle prickings, at least 36 percent of HIV/AIDS cases and more than 50 percent of Hepatitis B and Hepatitis C cases in the United States may be linked to the sharing of needles among drug addicts. Accordingly, there is a need to curb the practice of sharing needles among drug addicts.

The problem of needle sharing or needle reuses is further amplified when viewed in relation to the world population. For example, approximately 30 percent of reported HIV/AIDS cases in Brazil, Chile, Uruguay, Paraguay and Argentina are directly related to the sharing of contaminated needles among drug addicts. Approximately 70 percent of the HIV cases reported in China are directly linked to the sharing of contaminated needles. In eastern European countries, 80 percent of injection drug addicts admit to sharing contaminated needles. Approximately 43 percent of HIV/AIDS cases reported in Poland and Yugoslavia are linked to the sharing of contaminated needles among drug addicts.

Accidental needle prickings also pose a threat to healthcare workers. In particular, approximately one million accidental needle prickings are reported by healthcare workers in the United States annually. However, it is believed that at least three million accidental needle prickings occur each year, of which about two million are unreported. Various studies estimate that out of all the accidental needle pricking injuries that occur to nurses, approximately 40 percent to 53 percent go unreported. Various studies also estimate that out of all the needle pricking injuries that occur to laboratory technicians, approximately 92 percent go unreported. Various studies further estimate that out of all the needle pricking injuries that occur to physicians, approximately 70 percent to 95 percent go unreported.

In 1997, the Center for Disease Control and Prevention (CDC) sponsored a study that found that approximately 76 percent of needle pricking injuries could be avoided by using safety needles. Presently, there are at least 250 types of safety syringes. Unfortunately, the retractable safety syringes that currently exist have been criticized for various problems associated in operating the retractable safety syringe and its ineffectiveness.

One type of safety syringe is a vacuum assisted safety syringe wherein the needle of the syringe is retracted into a syringe body after a piston engages a needle holder due to a retraction force of a variable vacuum compartment. The retraction force of the variable vacuum compartment is a function of the surface area of the piston as it is traversed from a retracted position to an engaged position. Various types of seals may be used to create an airtight barrier around the plunger shaft. The seal or seals used to produce the variable vacuum compartment may begin to break down, become less resilient, or otherwise fail over time or due to various environmental conditions. For example, when various components of a syringe, such as the seal, are exposed to a prolonged force, the components may conform to an undesirable shape thereby reducing the effectiveness of the component and hamper the overall operation and function of the syringe. Additionally, the seals, or other components, of some safety syringes are prone to react negatively to hot climates. The exposure of these syringes to hot temperatures, cold temperatures, or temperature cycling during storage or shipment can lead to an operational failure of the syringe.

Furthermore, it is often desirable to prefill a safety syringes during an automated process prior to shipment. The process of manufacturing prefilled syringes typically includes sterilizing the syringe. The prefilled and sterilized syringe may then be shipped via at least one air shipment. If the shipment of prefilled syringes is shipped a long distance, such as to a developing country, the shipment of prefilled syringes may be carried via numerous air shipments. During the air shipment of the prefilled syringe the prefilled syringe may be exposed to numerous changes in atmospheric pressures. In some cases, shipping a prefilled syringe via air may exposed the syringe to a reduced pressure equivalent to an elevation of approximately 8,000 feet. If a gas bubble is present in the fluid chamber of the syringe, the gas bubble may increase in volume due to the decreased atmospheric pressure. As the gas bubble increases in volume, the stopper of the syringe may be proximally displaced, which may ultimately cause a sterility failure in the syringe. When the syringe returns to normal atmospheric conditions, the gas bubble returns to its starting volume and the stopper will return to its original location. Thus, a visual inspection of the stopper may not indicate stopper movement has occurred and a sterility failure may have transpired during shipment.

Accordingly, there is a need in the art for an improved safety syringe.

SUMMARY

One example embodiment of the present invention is a retractable safety syringe for preventing accidental needle pricking and needle reuse after completion of an injection stroke. The syringe may include a syringe body defining a proximal portion and a distal portion, A seal may be located in the proximal portion of the syringe body. A needle may be coupled to a needle holder, the needle holder removeably engageable to the body distal portion. A piston disposed within the body is biasable to the body proximal portion via a vacuum force when the piston is traversed toward the body distal portion, the piston being traversable between a retracted position and an engaged position. A vacuum chamber disposed within the syringe body may be located intermediate the piston and the seal, the vacuum chamber configured to provide a vacuum force on the piston in a direction from the syringe body distal portion toward the syringe body proximal portion upon movement of the piston toward the syringe body distal portion responsive to the distal translation of the piston. A fluid chamber may be disposed within the syringe body, the fluid chamber located distally from the piston, the fluid chamber having a distal and proximal end, the proximal end of the fluid chamber being sealed, the fluid chamber in fluid communication with the needle through the distal end of the fluid chamber and configured to be reduced in volume as the piston is traversed towards the engaged position. A shaft may be attached to the piston and disposed within the body, the shaft comprising an engaging portion and a non-engaging portion, the shaft extending through the proximal portion of the body and proximate the seal, traversal of the shaft though the body operative to traverse the piston within the syringe body between a storage position and working positions, the engaging portion proximate the seal and in sealing engagement with the seal in the working positions and the non-engaging portion proximate the seal and in a substantially non-sealing engagement with the seal in the storage position. Optionally, the engaging portion has a first outer diameter and the non-engaging portion has a second outer diameter, wherein the first outer diameter is greater than the second outer diameter. The shaft may optionally include a beveled transition between the engaging portion and the non-engaging portion.

The example syringe may optionally further have first cavity positioned proximate the body proximal portion and a brake member disposed in the first cavity of the body, the brake member proximate the non-engaging portion and in a substantially non-frictional engagement with the brake when the shaft is in the storage position, the brake member biased toward and frictionally engaged to the engaging portion for providing a braking force to maintain a position of the piston within the syringe body before completion of the injection stroke when the shaft is in the working positions, the brake member completely disengaged from the shaft after completion of the injection stroke by axially traversing the brake member into the second cavity so the vacuum force withdraws the needle into the syringe body to prevent accidental needle pricking and needle reuse. Optionally, the non-engaging portion is positioned intermediate the piston and the engaging portion; the non-engaging portion may optionally be less than about 0.5 inches in length along a longitudinal axis of the shaft. The engaging portion may further include a first engaging portion and a second engaging portion, wherein the non-engaging portion is disposed intermediate the first engaging portion and the second engaging portion, and wherein the second engaging portion is positioned intermediate the piston and the non-engaging portion.

Optionally, the first engaging portion is less than about 1 inch in length along a longitudinal axis of the shaft.

Optionally, the shaft may include a first beveled transition between the first engaging portion and the non-engaging portion and a second beveled transition between the non-engaging portion and the second engaging portion.

Optionally, the first engaging portion may be proximate the seal and in sealing engagement with the seal in the working positions. Optionally, the piston is substantially maintained in a stationary position when the piston is in the storage position.

Another example embodiment is a retractable safety syringe for preventing accidental needle pricking and needle reuse after completion of an injection stroke. The syringe may include a syringe body having a cavity and defining a proximal portion and a distal portion. A seal located may be in the proximal portion of the syringe body. A brake member may be disposed in the cavity of the body. A needle may be coupled to a needle holder, the needle holder removeably engageable to the body distal portion. A piston may be disposed within the body and biasable to the body proximal portion via a vacuum force when the piston is traversed toward the body distal portion, the piston being traversable between a retracted position and an engaged position. A vacuum chamber may be disposed within the syringe body, the vacuum chamber located intermediate the piston and the seal, the vacuum chamber configured to provide a vacuum force on the piston in a direction from the syringe body distal portion toward the syringe body proximal portion upon movement of the piston toward the syringe body distal portion responsive to the distal translation of the piston. A fluid chamber may be disposed within the syringe body, the fluid chamber located distally from the piston, the fluid chamber having a distal and proximal end, the proximal end of the fluid chamber being sealed, the fluid chamber in fluid communication with the needle through the distal end of the fluid chamber and configured to be reduced in volume as the piston is traversed towards the engaged position. A shaft may coupled to the piston and disposed within the body, the shaft comprising an engaging portion, a first non-engaging portion, and a second non-engaging portion, and extending through the proximal portion of the body and proximate the seal, traversal of the shaft though the body operative to traverse the piston within the syringe body between a storage position and working positions, the engaging portion proximate the seal and in sealing engagement with the seal in the working positions; the first non-engaging portion proximate the seal and in a substantially non-sealing engagement with the seal in the storage position, and the second non-engaging portion proximate the brake member and in a substantially non-frictional engagement with the brake when the shaft is in the storage position.

Optionally, the engaging portion has a first outer diameter, the first non-engaging portion has a second outer diameter, and the second non-engaging portion has a third outer diameter, wherein the first outer diameter is greater than each of the second and third outer diameters.

Optionally, the engaging portion may include an intermediate engaging portion disposed intermediate the first non-engaging portion and the second non-engaging portion.

Optionally, the engaging portion comprises a distal engaging portion positioned intermediate the piston and the first non-engaging portion.

Optionally, the distal engaging portion is less than about 1 inch in length along a longitudinal axis of the shaft.

Optionally, the shaft may include a first beveled transition between the non-engaging portion and intermediate engaging portion, a second beveled transition between the intermediate engaging portion and the second non-engaging portion, and a third beveled transition between the second non-engaging portion and the engaging portion.

Optionally, the an angle of at least one of the first and second beveled transitions is greater than the angle of the third beveled transition.

Optionally, the piston is substantially maintained in a stationary position when the piston is in the storage position.

Another example embodiment of the present invention is a method of operating an automatically retracting syringe. The method may include receiving a having the features of one the example embodiments described above, depressing a thumb platform to traverse the piston toward the distal portion of the syringe during an injection stroke; inducing a biasing force on the piston via the vacuum chamber to urge the piston assembly back toward the retracted position; engaging the piston to the needle holder upon completion of the injection stroke; disengaging the needle holder from the syringe body; removing thumb pressure on the thumb platform; and traversing the needle holder, and the needle into the syringe body under the biasing force.

Optionally, the method may further include distally translating the non-engaging portion away from the seal when the thumb platform is depressed. Optionally, the fluid chamber is at least partially filled with fluidic medication when the syringe is received.

Another example embodiment of the present invention is a retractable safety syringe for preventing accidental needle pricking and needle reuse after completion of an injection stroke. The syringe may include means for holding a volume of fluidic medication; means for expelling the fluidic medication from the holding means through a needle, wherein the expelling means is moveable between a first position and a second position; means for sealing a vacuum chamber; means for preventing a substantial load on the sealing means when the expelling means is in the first position; and means for engaging the sealing means in a sealed engagement when the expelling means is in the second position.

Optionally the example syringe may further include means for braking the expelling means; means for preventing a substantial load on the braking means when the expelling means is in the first position; and means for engaging the braking means in a frictional engagement when the expelling means is in the second position.

BRIEF DESCRIPTION OF THE DRAWINGS

The present invention will be more readily understood from a detailed description of example embodiments taken in conjunction with the following figures:

FIG. 4 is a perspective view of a piston of a retractable safety syringe in accordance with on non-limiting embodiment.

FIG. 5 is a cross-sectional view of the piston of FIG. 4

FIGS. 7-8 illustrate shafts of a retractable safety syringe in accordance with non-limiting embodiments.

FIGS. 9-19 illustrate enlarged views of the distal end of shafts in accordance with non-limiting embodiments.

FIGS. 16A and 16B illustrate a cross-sectional view of a portion of a retractable safety syringe in a storage position (FIG. 16A) and a working position (FIG. 16B).

FIGS. 17A and 17B illustrate a cross-sectional view of a portion of a retractable safety syringe in a storage position (FIG. 17A) and a working position (FIG. 17B).

FIGS. 18 and 19 illustrate a cross-sectional view of a portion of a prefilled retractable safety syringe in a storage position.

DETAILED DESCRIPTION OF EXAMPLE EMBODIMENTS

It will be appreciated that the terms "proximal" and "distal" may be used throughout the specification with reference to a medical professional or user utilizing a syringe to deliver medication to a patient. The term "proximal" refers to the portion of the syringe closest to the medical professional or user and the term "distal" refers to the portion located furthest from the medical professional or user. It will be further appreciated that for conciseness and clarity, spatial terms such as "vertical," "horizontal," "up," and "down" may be used herein with respect to the illustrated embodiments. However, syringes may be used in many orientations and positions, and these terms are not intended to be limiting and absolute.

Figure 1:
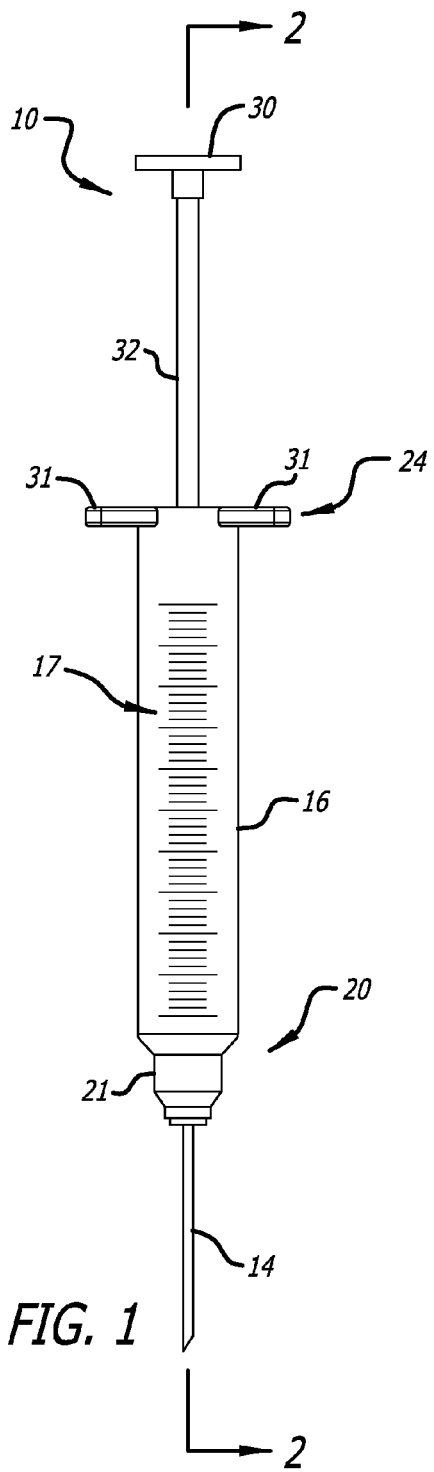
FIG. 1 is a side view of a retractable safety syringe in accordance with one non-limiting embodiment.
Figure 2:
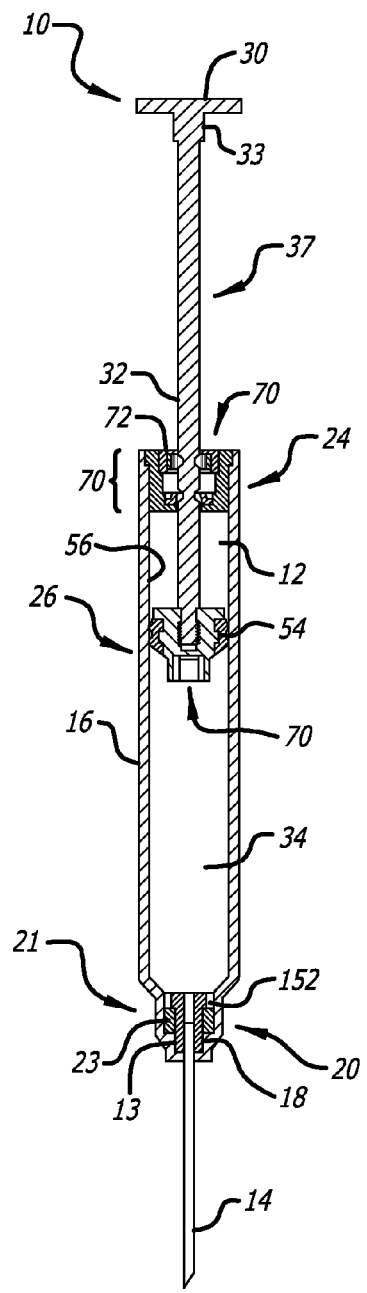
FIG. 2 is a cross-sectional view of the retractable safety syringe of FIG. 1.

FIGS. 1-2 illustrate a retractable safety syringe 10 in accordance with one non-limiting embodiment. FIG. 1 is a side view of the retractable safety syringe 10. FIG. 2 is a cross sectional view of the retractable safety syringe of FIG. 1 taken along Line 2-2. The retractable safety syringe 10 has a vacuum chamber 12 that creates a retraction force to retract a needle 14 of the retractable safety syringe 10 within the retractable safety syringe 10 so as to prevent accidental needle pricking and needle reuse. The retractable safety syringe 10 may have a syringe body 16 defining a distal portion 20 and a proximal portion 24. The body 16 may define a fluid chamber 34 fillable with fluidic medication. As discussed in more detail below, the retractable safety syringe 10 may be configured as a prefilled syringe. A needle holder 18 may be removably engaged to the distal portion 20 of the syringe body 16. The needle 14 may be fixedly engaged to the needle holder 18 and protrude coaxially out of the distal portion 20 of the syringe body 16. The fluid chamber 34 is in fluid communication with the needle 14 through the distal end of the fluid chamber 34. The retractable safety syringe 10 may also have a plunger assembly 37 comprising a piston 26 coupled to a rigid shaft 32. In various embodiments, the shaft 32 may having a plurality of components assembled together to form the shaft. In various embodiments, the shaft 32 may be unitary with the piston 26. In various embodiments, the shaft 32 may be joined to the piston 26 via a threaded engagement, although this disclosure is not so limited. The piston 26 may have a punch 70 distally protruding toward the needle holder 18. The plunger assembly 37 is traversable within the syringe body 16 between a retracted position and an engaged position. Generally, the retracted position is when the piston 26 is closer to the proximal portion 24 of the syringe body 16 than the distal portion 20 of the syringe body 16. But, the retracted position may include situations when the piston 26 does not contact the needle holder 18 and the piston 26 is closer to the distal portion 20 of the syringe body 16 than the proximal portion 24 of the body 16. The engaged position is when the piston 26 is in contact with the needle holder 18 and engaged to the needle holder 18.

The shaft 32 may extend out of the syringe body 16 through the proximal portion 24 of the syringe body 16 and may be coaxially aligned with the syringe body 16. A thumb platform 30 may be attached to the proximal portion of the shaft 32. The thumb platform 30 may be operative to traverse the plunger assembly 37 between the retracted position and the engaged position. The retractable safety syringe 10 may also finger platforms 31 extending laterally from the proximal portion 24.

A wedge element 152 may be positioned between the needle holder 18 and the distal portion 20 to form an airtight and fluid tight seal therebetween. In particular, the distal portion 20 of the body 16 may have a cylindrical nub 21. The needle holder 18 may a corresponding configuration as an inner surface 23 of the cylindrical nub 21. The needle holder 18 may have a lip 13 (see FIG. 2) to engage the distal portion 20 such that the needle holder 18 is not pushed out the distal portion 20 of the body 16 as a wedge element 152 is traversed to the releasing position (discussed below).

Various portions of the body 16 may be transparent to allow viewing of the fluidic medication by the user. Furthermore, a marked portion 17 may also have volume markings, or other indicia, to indicate volume levels within the fluid chamber 34. The aspect ratio (i.e., the ratio of the height to the width) of the fluid chamber 34 for any particular retractable safety syringe 10 may vary based on the intended volume of medication to be dispensed. For neonatal embodiments, for example, the aspect ratio of the fluid chamber 34 may be configured to provide the proper resolution to dispense medication in extremely small dosages (e.g., less than 1 cc, or less than 0.5 cc). In other embodiments, the aspect ratio of the fluid chamber 34 may be configured to dispense medication in larger dosages (e.g., more than 1 cc).

The piston 26 may have an outer diameter similar to the inner diameter of the body 16. The piston 26 may have a piston seal 54 which engages an outer surface of the piston 26 and an inner surface 56 of the body 16. The piston seal 54 may form a watertight and an airtight seal between the piston 26 and the inner surface 56 of the body 16, thus maintaining a barrier between the fluid chamber 34 from the vacuum chamber 12. The piston seal 54 may traverse along the inner surface 56 of the body 16 as the plunger assembly 37 is traversed between the retracted position and the engaged position.

Figure 3:
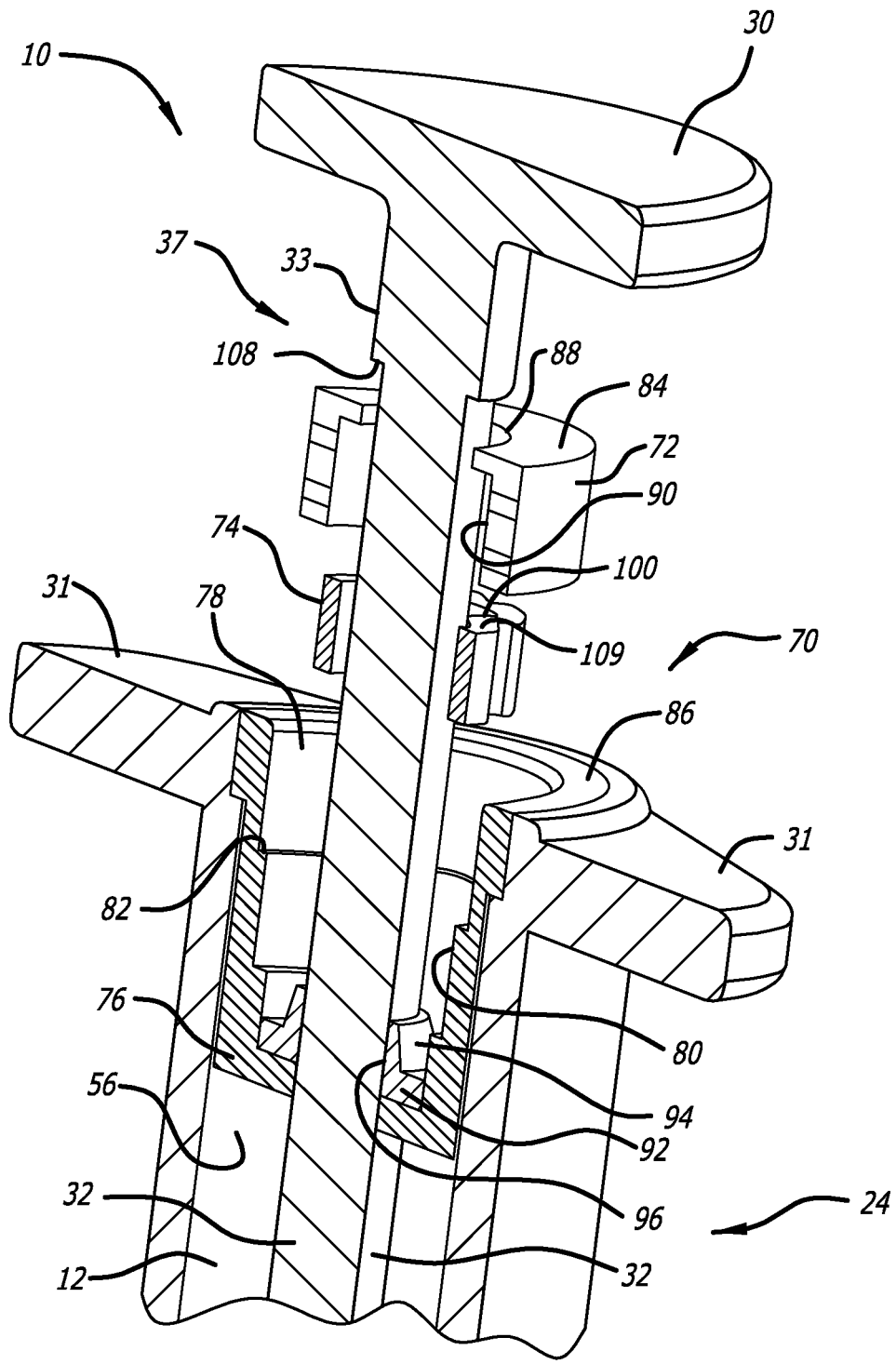
FIG. 3 is a cross sectional perspective view of the distal end of the retractable safety syringe with an exploded view of a braking mechanism in accordance with one non-limiting embodiment.

In various embodiments, the retractable safety syringe 10 may further have a braking mechanism 70 disposed at the proximal portion 24 that holds the plunger assembly 37 in place between the retracted position and a filling position prior to engagement of the piston 26 with the needle holder 18. The filling position when the plunger assembly 37 is between the engaged position and the retracted position and the piston 26 is closely adjacent the needle holder 18. By way of example and not limitation, the filling position may be when the piston 26 is in contact with the needle holder 14 but not engaged to the needle holder 14. FIG. 3 is a cross sectional view of the distal end of the retractable safety syringe 10 illustrating an exploded view of the braking mechanism 70 in accordance with one non-limiting embodiment. With reference to FIGS. 2 and 3, the braking mechanism 70 permits the retractable safety syringe 10 to be operated in a substantially similar manner to prior art non-retracting conventional syringes except that the syringe 10 automatically retracts the needle 14 into the body 16 immediately after fluidic medication has been injected into a patient or user. In prior art non-retracting safety syringes, the piston does not traverse back toward the retracted position when thumb pressure is released from the thumb platform. The reason is that prior art non-retracting safety syringes do not have a retraction force acting on the piston. In the illustrated embodiment, the plunger assembly 37 does not traverse back toward the retracted position when thumb pressure is released from the thumb platform 30 because of the braking mechanism 70. The braking mechanism 70 of retractable safety syringe 10 counteracts the refraction force of the vacuum chamber 12 such that the needle 14 does not automatically retract when thumb pressure is released from a thumb platform 30.

The braking mechanism 70 may have a cover 72 and a brake member 74 that are engaged to an attachment base 76. The attachment base 76 may define an inner surface that has a stepped configuration. An upper step 78 may have a larger inner diameter compared to an inner diameter of a lower step 80. The upper step 78 and the lower step 80 may be joined to each other via a lip 82. The cover 72 may have an outer diameter sized to fit the upper step 78. Also, a top surface 84 of the cover 72 may be flush with a top surface 86 of the attachment base 76. The cover 72 may be fixedly attached to the attachment base 76 via sonic welding, adhesive and other joining methods known in the art. The attachment base 76 may be fixedly attached to the proximal portion 24 using any suitable joining technique known in the art, such as spin welding, for example. The cover 72 may have a through-hole 88 through which the shaft 32 may be disposed and slidingly traversed. An inner surface 90 of the cover 72 may have an inner diameter that is smaller than the inner diameter of the lower step 80.

The brake member 74 may be disposed and frictionally engaged to the cover 72. The brake member 74 may be split into two or more pieces. In one embodiment, the brake member 74 is split into two pieces that are mirror configurations of each other. When the brake member 74 is disposed in the cover 72, an outer diameter of the brake member 74 may be equal to or slightly greater than the inner diameter of the inner surface 90 of the cover 72. In this manner, the brake member 74 frictionally engages the cover 72 and the inner surface 90 of the cover 72 biases the brake member 74 inwardly toward the shaft 32. The amount of inward bias may be pre-set by changing the relative sizes of the inner diameter of the cover 72 and the outer diameter of the brake member 74.

The attachment base 76 may also house a shaft seal 92. In one embodiment, the shaft seal 92 has a longitudinal flange 94 defining a through-hole 96 through which the shaft 32 may be disposed and slidingly traversed. In other embodiments, other types of seals known in the art may be used for the shaft seal 92, such as an o-ring or a wiper seal, for example. In some embodiments, a combination of seals may be used to form the shaft seal 92. When the shaft 32 is in the working positions, as discussed in more detail below, the shaft seal 92 forms an airtight seal with the shaft 32 in order to maintain a vacuum in the vacuum chamber 12 when the piston 26 is traversed distally from the attachment base 76. The longitudinal flange 94 of the shaft seal 92 may flex to expand or contract the through-hole 96 in order to maintain contact with the shaft 32.

When the brake member 74 is disposed in the cover 72, the brake member 74 is in a braking position. At the braking position, the brake member 74 may have a plurality of fingers or projections 100 that inwardly protrude toward the shaft 32. The inner surface 88 of the cover 72 biases the projections 100 inwardly, and the projections 100 press against the outer surface of the shaft 32 inducing a frictional force between the projections 100 of the brake member 74 and the outer surface of the shaft 32. Alternatively, it is also contemplated that the brake member 74 may have a cylindrical inner surface, or any other suitably shaped surface. The entire inner surface of the brake member 74 may contact or press against the outer surface of the shaft 32. Accordingly, it is contemplated that the friction surface of the brake member 74 that presses against the outer surface of the shaft 32 may have other configurations to change the amount of inward bias. It is also contemplated the amount of friction force between the brake member 74 and the outer surface of the shaft 32 may be varied to meet the requirements of the syringe. For example, the inner diameter of the inner surface 90 of the cover 72 may be reduced so as to further bias the projections 100 against the outer surface of the shaft 32. The friction force between the brake member 74 and the shaft 32 may also be varied by changing the material of the brake member 74 and the shaft 32 or having different finishes at the interface of the outer surface of the shaft 32 and the friction surface of the brake member 74. During operation, when the brake member 74 is at the braking position (see FIGS. 16B and 17B), the friction force between the projections 100 of the brake member 74 and the shaft 32 is less than the friction force between the brake member 74 and the cover 72. In this manner, the brake member 74 is not dislodged out of the cover 72 and within the lower step 80 (e.g., released position) as the plunger assembly 37 is traversed toward the filling position or engaged position. The shaft 32 may slide against the projections 100 of the brake member 74 as the plunger assembly 37 is traversed between the refracted position and the engaged position without the brake member 74 being dislodged from the braking position due to the frictional forces of the projections 100 of the brake member 74 and the shaft 32 being less than the frictional forces of the brake member 74 and cover 72.

The brake member 74 is traversable between the braking position and a released position. When the brake member 74 is traversed to the released position (see FIG. 6), the brake member 74 is disposed within the lower step 80 of the interior cavity of the attachment base 76. The inner surface 90 of the cover 72 no longer biases the projections 100 inwardly to press the projections 100 of the brake member 74 against the shaft 32 creating the frictional force that counteracts the retraction force of the vacuum chamber 12. At the released position, the brake member 74 is loose because the lower step 80 defines a larger volume and the brake member 74 such that the brake member 74 falls apart, or otherwise expands, when disposed within the lower step 80. The projections 100 do not press against the outer surface of the shaft 32 and does not produce any counteracting forces such that the plunger assembly 37 may be freely retracted toward the retracted position when the user releases the thumb platform 30.

To traverse the brake member 74 from the braking position to the released position, the plunger assembly 37 may be formed with a ram 33 which initially contacts an upper surface 109 (see FIG. 3) of the brake member 74 and pushes the brake member 74 out of the cover 72 and within the lower step 80. More particularly, when the plunger assembly 37 is traversed toward the engaged position, a lower surface 108 of the ram 33 contacts the upper surface 109 of the brake member 74. As the plunger assembly 37 is further traversed to the engaged position, the ram 33 continues to push downwardly on the brake member 74 urging the brake member 74 off of the inner surface 90 of the cover 72 and within the lower step 80. An outer diameter of the ram 33 may be smaller than an inner diameter of the through-hole 88 of the cover 72 such that there is no frictional engagement between the ram 33 and the cover 72. As shown in FIGS. 1-3, the ram 33 may be integrally formed with the shaft 32 and the thumb platform 30 such that the ram 33 is formed as part of the plunger assembly 37 in general. In some embodiments, the ram 33 may be formed with the thumb platform 30, and the thumb platform 30 may have a receiver portion that receives a proximal portion of the shaft 32.

In use, the braking mechanism 74 prevents the plunger assembly 37 from retracting toward the retracted position during operation of the syringe as long as the brake member 74 is maintained at the braking position. The user may release the thumb platform 30 without any concern that the plunger assembly 37 will be traversed back toward the refracted position The retractable safety syringe 10 may be prefilled and shipped and ultimately provided to a medical professional or user with the plunger assembly 37 in a storage position (as shown in FIG. 2) with fluidic medication contained within the variable fluid chamber 34. Alternatively, the retractable safety syringe 10 may be shipped and ultimately provided to a medical professional or user with the plunger assembly 37 in a storage position (see FIGS. 16A and 17A) without fluidic medication contained within the variable fluid chamber 34.

Figure 6:
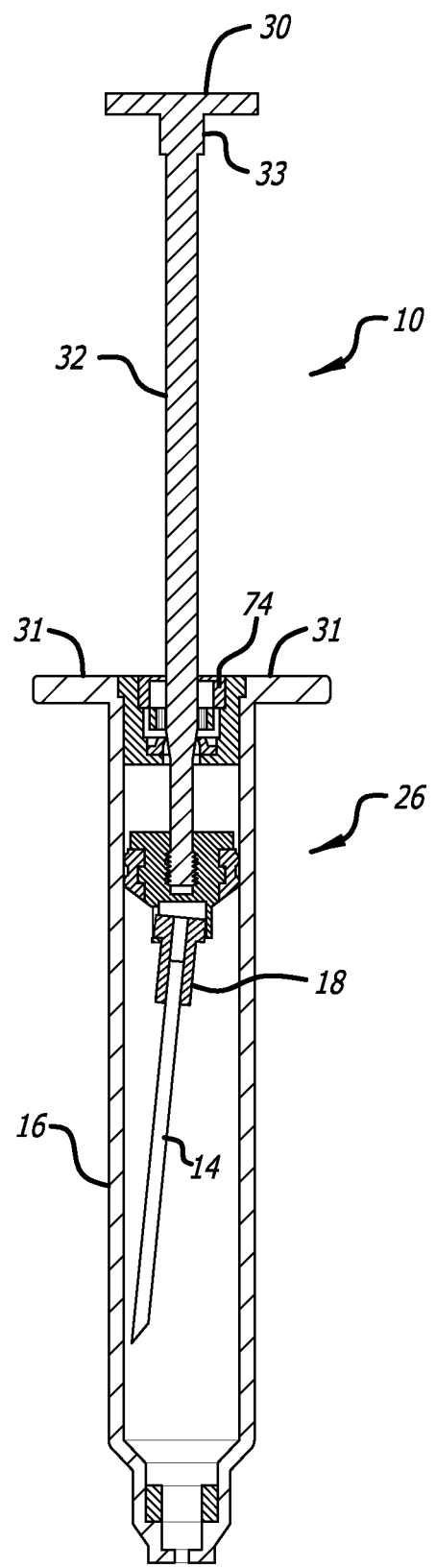
FIG. 6 illustrates a retractable safety syringe at the conclusion of the operational stroke.

FIG. 4 is a perspective view of the piston 26 in accordance with one non-limiting embodiment. FIG. 5 is a perspective view of the piston 26 of FIG. 4 taken along a longitudinal axis (illustrated as "A"). Referring now to FIGS. 2, and 4-5, by way of example and not limitation, when the needle holder 18 is engaged to the distal portion 20, a wedge element 152 may be in frictional contact with the needle holder 18. The piston 26 may have a punch 70 distally protruding toward the needle holder 18. The punch 70 may be a substantially hollow cylinder. In one embodiment the punch 70 is equipped with an upper proximal block tab 73 extending around less than about one-half of the circumference of the substantially hollow cylinder, and a lower distal wedge tab 75 extending around less than about one-half of the circumference of the substantially hollow cylinder and located opposite the upper block tab 73. During the engagement process, the punch 70 may distally push the wedge element 152 and engage the needle holder 18. The lower distal wedge tab 75 passes and hooks onto the needle holder 18 (e.g., a lip of the needle holder) when the plunger assembly 37 is traversed to the engaged position. After engagement, the needle body 18 and needle 14 are withdrawn into the syringe body 16 via the retraction force. The punch 70 may also define a cutout 71 positioned longitudinally proximal to upper proximal block tab 73 and a ramp 77 positioned longitudinally proximal to lower distal wedge tab 75. When the needle body 18 and the needle 14 are refracted, the ramp 77 may laterally bias the needle body 18 and the cutout 71 may receive a portion of the needle body 16 to cant the needle 16 toward one side of the syringe body 16. FIG. 6 illustrates a retractable safety syringe 10 at the completion of the operational stroke.

FIGS. 7-8 illustrate the shaft 32 in accordance with various non-limiting embodiments. The shaft 32 illustrated in FIGS. 7-8 may be used, for example, with a prefilled syringe. The shaft 32 may have a threaded portion 40 to engage the piston 54 (FIG. 2). The shaft 32 has an engaging portion 42 and a non-engaging portion 44. As illustrated, the engaging portion 42 may be discontinuous along the longitudinal axis. For example, the engaging portion 42 may comprise a first engaging portion 42a and a second engaging portion 42b. The non-engaging portion 44 may also be discontinuous along the longitudinal axis. For example, the non-engaging portion 44 may comprise a first non-engaging portion 44a and a second non-engaging portion 44b (FIG. 7). A third engaging portion 44c may be positioned intermediate the first non-engaging portion 44a and the second non-engaging portion 44b.

The engaging portion 42 has an outer diameter that is sized to engage the shaft seal 92 (FIG. 2) and form an airtight barrier when the engaging portion 42 is positioned proximate the shaft seal 92. The outer diameter of the engaging portion 42 may be at least slightly greater than the inner diameter of the through-hole 96 (FIG. 2) of the shaft seal 92. The engaging portion 42 is also sized to frictionally engage the brake member 74 when the engaging portion 42 is positioned proximate the brake member 74. Thus, the engaging portion 42 is generally the portion of the shaft 32 that either engages the shaft seal 92 or frictionally engages the brake member 74. The non-engaging portion 44 has an outer diameter that is sized such that an airtight seal is not formed (e.g., a non-sealing engagement) when positioned proximate the shaft seal 92 (FIG. 2). The outer diameter of the non-engaging portion 44 may be less than the inner diameter of the through-hole 96 (FIG. 2) of the shaft seal 92. In some embodiments, the outer diameter of the non-engaging portion 44 is substantially similar to the inner diameter of the through-hole 96 of the shaft seal 92 such that only nominal contact is made between the shaft seal 92 and non-engaging portion 44, but an airtight seal is not formed. The non-engaging portion 44 is also sized such that there is no frictional engagement, or at least only a minimal frictional engagement between the brake member 74 and the non-engaging portion 44 when the engaging portion 42 is positioned proximate the brake member 74. As discussed in more detail below, by limiting the amount of force exerted on the shaft seal 92 and the brake member 74, the shelf life of the retractable safety syringe 10 is extended. Since the syringe 10 may be stored with little or no-load on sensitive internal components, the syringe 10 can also endure various environmental conditions during extended periods of storage (e.g., changes in temperature) without the components failing or otherwise deforming.

Still referring to FIGS. 7-8, the outer diameter of the non-engaging portion 44 is less than the outer diameter of the engaging portion 42. The particular diameters of these portions for any particular implementation may be at least partially dependent on the size of the associated syringe and the inner diameters of the shaft seal 92 and the brake member 74. For example in one non-limiting embodiment, the outer diameter of the engaging portion 42 may be about 0.125 inches and the outer diameter of the non-engaging portion 44 may be about 0.085 inches. In other embodiments, the outer diameter of the engaging portion 42 may be larger or smaller than 0.125 inches and the outer diameter of the non-engaging portion 44 may be larger or smaller than 0.085 inches. In some embodiments, the outer diameter of the engaging portion 42 may be a multiple of the outer diameter of the non-engaging portion 44. For example, in one embodiment, the outer diameter of the engaging portion 42 is at least 1.1 times the outer diameter of the non-engaging portion 44. In one embodiment, the outer diameter of the engaging portion 42 is at least 1.3 times the outer diameter of the non-engaging portion 44. In one embodiment, the outer diameter of the engaging portion 42 is at least 1.6 times the outer diameter of the non-engaging portion 44. In one embodiment, the outer diameter of the engaging portion 42 is at least 2 times the outer diameter of the non-engaging portion 44. In one embodiment, the outer diameter of the engaging portion 42 is at least 3 times the outer diameter of the non-engaging portion 44. In some embodiments, the outer diameters of the first engaging portion 42a and the second engaging portion 42b may differ. In some embodiments, the outer diameters of the first non-engaging portion 44a and the second non-engaging portion 44b may differ. Accordingly, this disclosure is not limited to any particular diameter configuration of non-engaging and engaging portions of the shaft.

Still referring to FIGS. 7-8, the non-engaging portion 44 may be longitudinally positioned along the shaft 32 at any suitable location, included the distal end of the shaft 32. As discussed in more detail below, the position of the non-engaging portion 44 may be based on the total volume of the fluid chamber 34 and amount of prefilled medication contained by the fluid chamber 34. As illustrated, the second engaging portion 42b may be positioned intermediate the non-engaging portion 44 and the piston 26 (FIG. 2). The longitudinal offset of the non-engaging portion 44 from the distal end of the shaft 32 may vary. In some embodiments, the non-engaging portion 44 is longitudinally positioned approximately 0.5 inches from the piston 26. Such an arrangement may be used, for example, with a 5 cc syringe that is prefilled with 3 cc of medication.

The retractable safety syringe 10 may shipped and/or stored when the plunger assembly 37 is in a storage position. In the storage position (see e.g., FIG. 2), the shaft 32 is not placing a potentially destructive load on either the shaft seal 92 or the brake member 74. Accordingly, the retractable safety syringe 10 can be stored in this position for relatively long periods of time without degradation or deformation of the components within the retractable safety syringe 10 that could affect the functionality of the syringe, thereby increasing its storage life. When a user either distally or proximally translates the plunger assembly 37, the plunger assembly 37 is moved out of the storage position and into the working positions. Thus, the working positions include all of the positions of the plunger assembly 37 that rely on a seal between the shaft 32 and the vacuum chamber 12 and/or a frictional engagement between the shaft 32 and the brake member 74 for proper operation. For example, the working positions of the plunger assembly 37 may include the various positions of the plunger assembly during the dispensing of the fluidic medication and the retraction of the needle 14 into the syringe body 16 via the vacuum retraction force. The length of the non-engaging portion may be at least slightly greater than the longitudinal separation of the shaft seal 92 and the brake member 74. For example, the non-engaging portion may be about 0.2" in length. In embodiments having multiple non-engaging portions 44 (FIG. 7), the sizing of each of the non-engaging portions 44 may depend on the size of the component that the non-engaging portion 44 is proximate too in the storage position. For example, for embodiments having a brake member 74 with a longitudinal dimension of about 0.12", the first engaging portion 42a may be longitudinally spaced from the third engaging portion 42c at a distance greater than 0.12". Similarly, for embodiments having a shaft seal 92 with a longitudinal dimension of about 0.07", the third engaging portion 42c may be longitudinally spaced from the second engaging portion 42b at a distance greater than 0.07". As is to be appreciated, in various embodiments, the spacing and arrangement of the engaging portions and non-engaging portions along the shaft may vary based on application.

Figure 9:
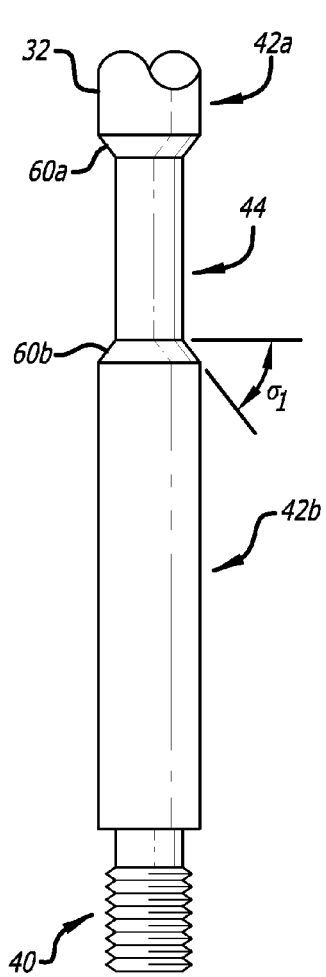
Figure 10:
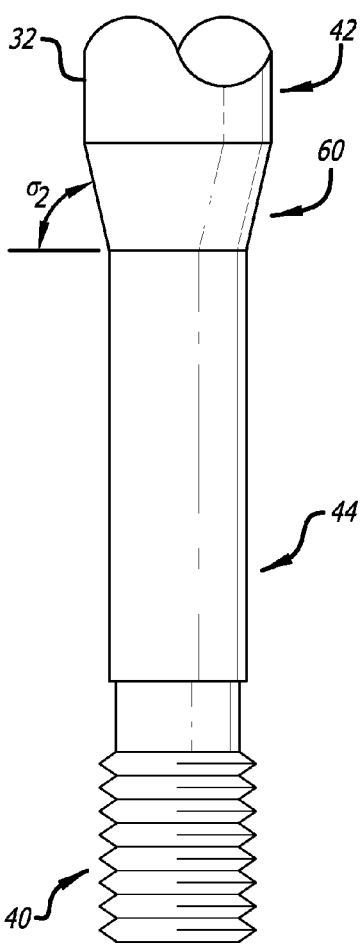

FIGS. 9-15 illustrated enlarged views of the distal end of the shaft 32 in accordance with various non-limiting embodiments. Referring to FIG. 9, the transitions between the non-engaging portion 44 and the engaging portions 42 may be beveled. According to various embodiments, the bevels (e.g., tapers) may comprise curved portions, linear portions, or a combination of curved and linear portions. The first bevel 60a serves as a transition from the first engaging portion 42a to the non-engaging portion 44 and a second bevel 60b serves as a transition from the non-engaging portion 44 to the second engaging portion 42b. The bevels 60 generally aid in the operation of the retractable safety syringe 10 as the plunger assembly 37 is translated between the storage position and the working positions. For example, the bevel 60 helps to reduce the likelihood that the engaging portion 44 undesirably dislodges the brake member 74 as the engaging portion 42a comes in contact with the brake member 74 during the operational stroke.

Figure 11:
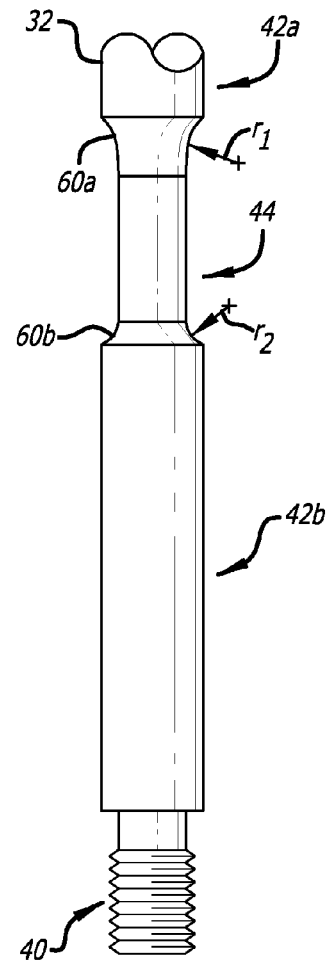

The angle of the bevel 60 may be any suitable angle. For example, $\theta_1$ (FIG. 9) may be approximately 50 degrees, although this disclosure is not so limited. In some embodiments, $\theta_2$ (FIG. 10) may be approximately 75 degrees, although this disclosure is not so limited. The particular angle of the bevel 60 may be based on, for example, manufacturing methods, the type of shaft seal 92, and/or the configuration of the brake member 74. FIG. 11 illustrates first and second bevels 60a, 60b that are generally curved in accordance with one non-limiting embodiment. The first bevel 60a has a curved section having a radius '$r_1$.' The second bevel 60b has a curved section having a radius '$r_2$.' In this embodiment the first bevel 60a provides for a more graduated transition between the first engaging portion 42a and the non-engaging portion 44 as compared to the second bevel 60b.

Figure 12:
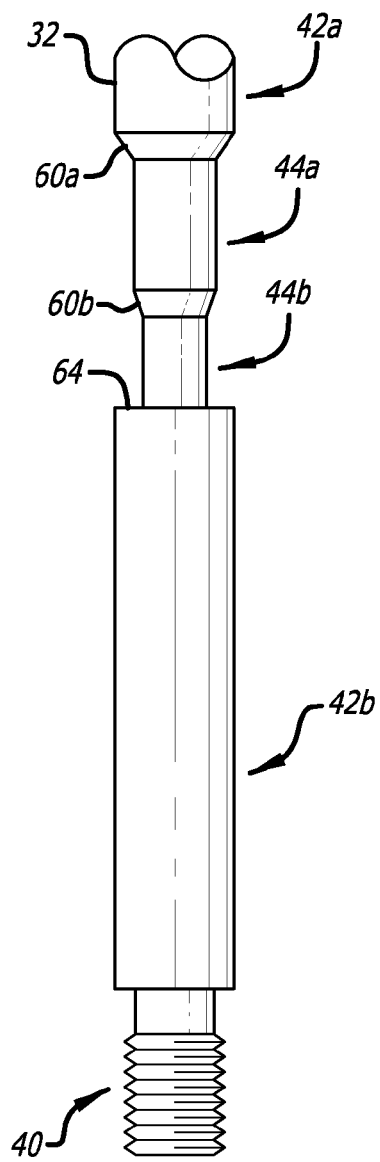
Figure 13:
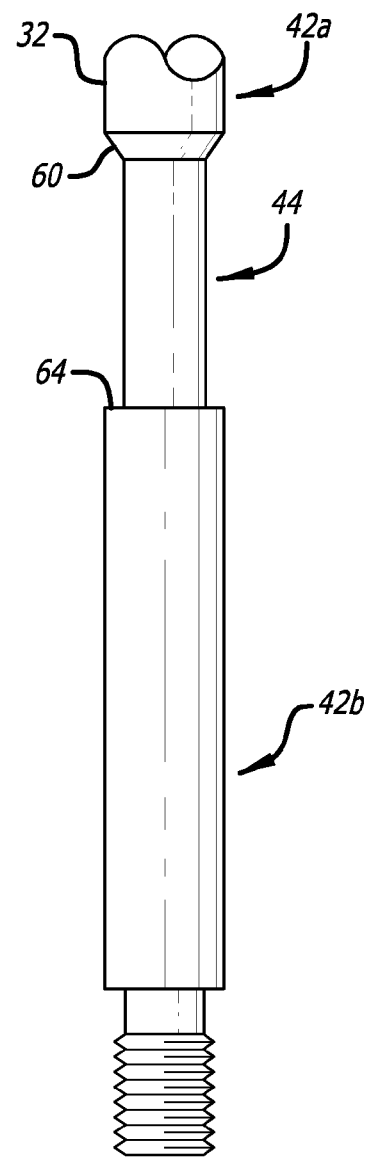
Figure 14:
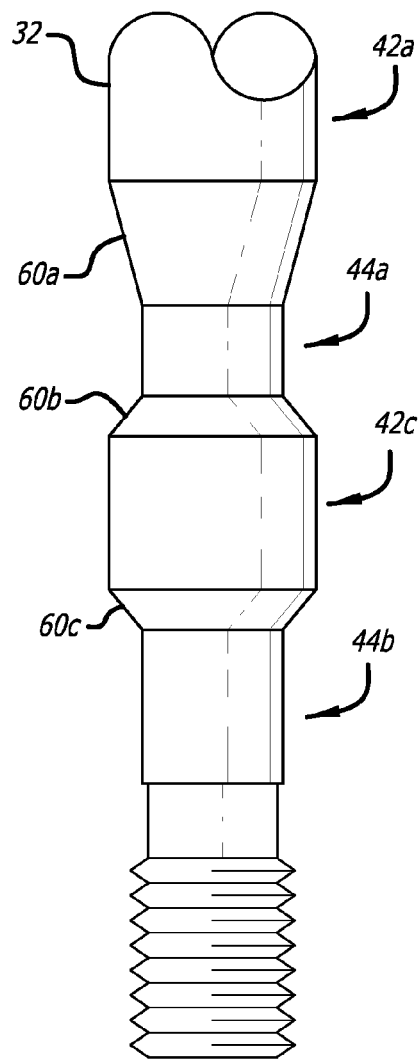
Figure 15:
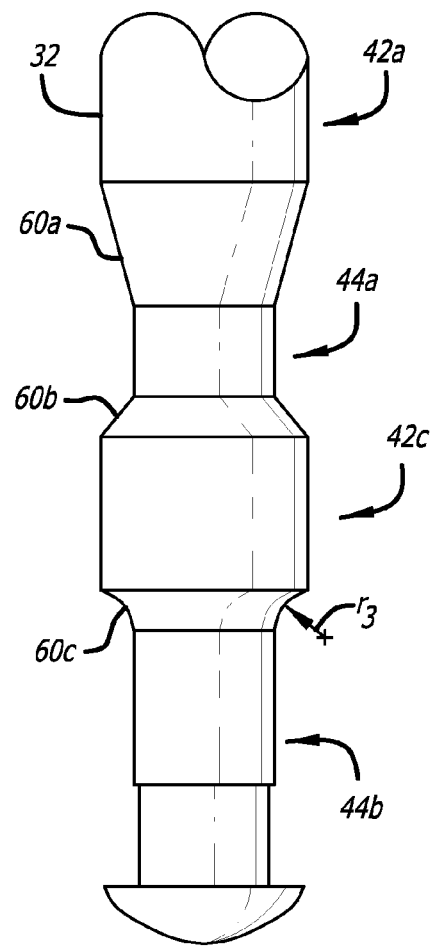

FIG. 12 illustrates the distal end of the shaft 32 in accordance with another non-limiting embodiment. The shaft 32 comprises a first non-engaging portion 44a having a larger outer diameter than a second non-engaging portion 44b. The shaft 32 has a first bevel 60a that transitions between the first engaging portion 42a and the first non-engaging portion 44a and a second bevel 60b that transitions between the first non-engaging portion 44a and the second non-engaging portion 44b. A lip 64 serves as the transition between the second non-engaging portion 44b and the second engaging portion 42b. FIG. 13 illustrates an embodiment of the shaft 32 comprising a bevel 60 transitioning between the first engaging portion 42a and a non-engaging portion 44 and a lip 64 serves as the transition between the non-engaging portion 44 and the second engaging portion 42b. FIGS. 14 and 15 illustrate embodiments of the shaft 32 that have the non-engaging portion 44 positioned proximate the distal end of the shaft 32. As illustrated, the bevels 60 may be any suitable configuration. For example, the first bevel 60a allows for a more gradual transition than the second bevel 60b. As illustrated in FIG. 15, the third bevel 60c is curved and has a radius '$r_3$.'

FIGS. 16A and 16B illustrate a cross-sectional view of a portion of the retractable safety syringe 10 in a storage position (FIG. 16A) and a working position (FIG. 16B) in accordance with one non-limiting embodiment. Referring first to FIG. 16A, the non-engaging portion 44 is proximate the shaft seal 92 and the brake member 74 while in the storage position. The shaft 32 and the shaft seal 92 do not form an air-tight seal (e.g., a non-sealing engagement) in the storage position. Therefore, the shaft 32 does not contact the shaft seal 92, or at least only nominally contacts the shaft seal 92 in this position. Similarly, the shaft 32 is not in frictional engagement with the brake member 74. If any contact is made between the brake member 74 and the non-engaging portion 44, it is only nominal such that it will not affect the performance of the brake member 74 if such contact is maintained for a long period of time. As is to be appreciated, the amount of contact between the shaft seal 92 and/or the brake member 74 may depending on the particular implementation of these components. For example, if the shaft seal 92 is an o-ring, the o-ring may be generally able to withstand a greater force than a molded wipe seal. Similarly, if the brake member 74 is hardened plastic, for example, it may be able to withstand more force than a resilient rubber brake member. In any event, the combination of components is arranged such that the retractable safety syringe 10 may be maintained in the storage position for relatively long periods of time, at various temperatures, and various atmospheric pressures, without substantial deformation of the shaft seal 92 and or the brake member 74. Therefore, when a user ultimately translates the shaft 32 after a period of storage, the seal 92 and brake member 74 will function properly.

Referring now to FIG. 16B, the retractable safety syringe 10 is illustrated in a working position after the plunger assembly 37 has been distally translated. In the working position, the engaging portion 42 is proximate the shaft seal 92 and the brake member 74. The engagement between the engaging portion 44 and the shaft seal 92 forms an airtight barrier for the vacuum chamber 12. The frictional engagement between the brake member 74 and the engaging portion 44 allows the user to remove their thumb from the thumb platform 30 (FIG. 2) without the plunger assembly 37 being drawn in the proximal direction due to the vacuum force of the vacuum chamber 12 upon the piston 26.

FIGS. 17A and 17B illustrate a cross-sectional view of a portion of the retractable safety syringe 10 in a storage position (FIG. 17A) and a working position (FIG. 17B) in accordance with one non-limiting embodiment. As illustrated, the shaft 32 has multiple non-engaging portions 44. In the storage position shown in FIG. 17A, the first non-engaging portion 44a is positioned proximate the brake member 74 and the second non-engaging portion 44b is proximate the shaft seal 92. By having an engaging portion 44c positioned intermediate the first non-engaging portion 44a and the second non-engaging portion 44b, incidental translation of the plunger assembly 37 may be eliminated, or at least reduced, while the syringe is in the storage position. Referring now to FIG. 17B, the retractable safety syringe 10 is illustrated in a working position after the plunger assembly 37 has been distally translated. In the working position, the engaging portion 42a is proximate the shaft seal 92 and the brake member 74 allowing for proper operation of the retractable safety syringe 10.

Figure 18:
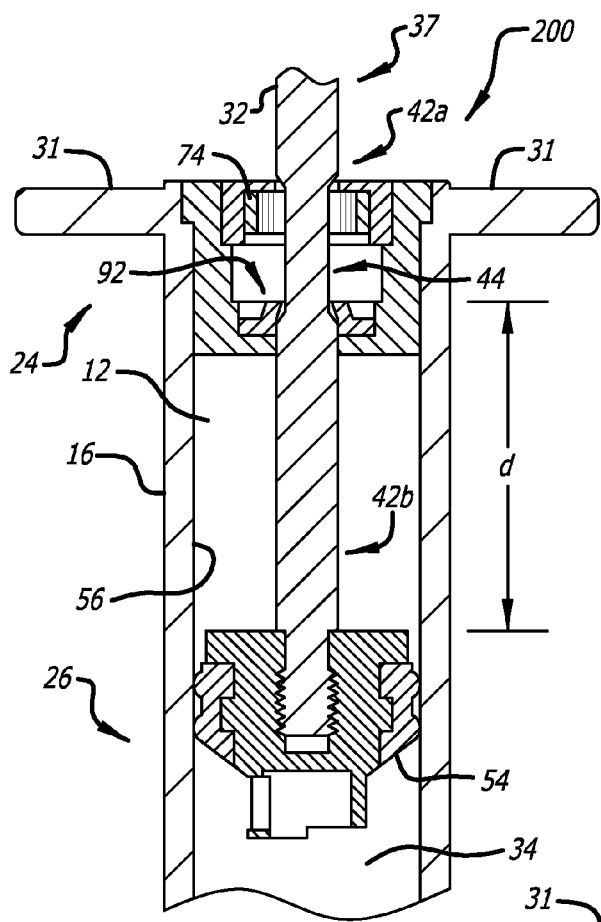

FIG. 18 illustrates a portion of a prefilled retractable safety syringe 200 in its storage position in accordance with one non-limiting embodiment. The prefilled retractable safety syringe 200 may be generally similar to the retractable safety syringe 10, accordingly similar reference numbers are used to identify similar components. The prefilled retractable safety syringe 200 may be shipped or stored with fluid in the fluid chamber 12 without the shaft seal 92 and the brake member 74 under a substantial load.

In this embodiment, the non-engaging portion 44 is proximally offset from the piston 26, similar to the shaft 32 illustrated in FIG. 8. The volume of the fluid chamber 34 when the prefilled retractable safety syringe 200 is in the storage position is therefore a function of the longitudinal distance (illustrated as 'd') between the piston 26 and the non-engaging portion 44 of the shaft 32. As the longitudinal distance 'd' increases, the volume of the fluid chamber 34 in the storage position will decrease. In various embodiments, the location of the non-engaging portion 44 along the shaft 32 is determined by the amount of fluidic medication that will be stored in the fluid chamber 34 during shipment. In any event, the syringe may be shipped with the piston 26 located at a position in between the proximal end 24 and the distal end 20, as opposed to being drawn toward the proximal end 24 of the prefilled retractable safety syringe 200.

By way of example, for a 5 cc syringe that will be shipped with 3 cc of medication, the longitudinal distance 'd' between the piston 26 and the non-engaging portion 44 will be a first distance. If the same syringe was to be shipped with 4 cc of medication, the longitudinal distance 'd' between the piston 26 and the non-engaging portion 44 will be a second distance, where the second distance is less than the first distance. As is to be appreciated, the longitudinal distance 'd' could still be similar between these two implementations if the diameter of the barrel 16 was increased for the 4 cc implementation.

While the plunger assembly 37 is in the storage position, the vacuum chamber 12 is generally at the same pressure as the atmospheric pressure since the shaft seal 92 is not in a sealing engagement with the shaft 32. Once the plunger assembly 37 is distally translated, an air-tight seal is formed between the engaging portion 42a and the shaft seal 92 to generate vacuum with in the vacuum chamber necessary for the proper operation of the prefilled retractable safety syringe 200

Figure 19:
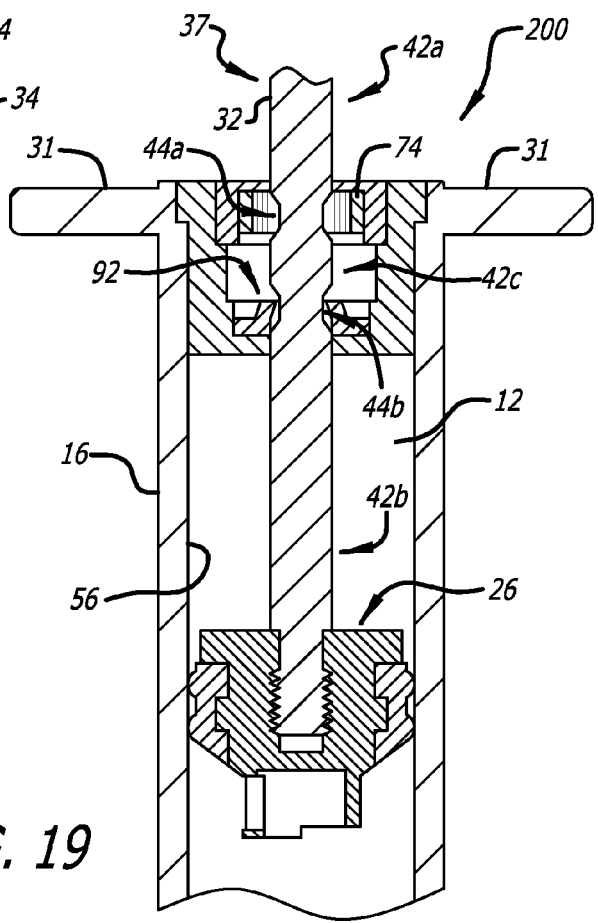

FIG. 19 illustrates another embodiment of the prefilled retractable safety syringe 200 shown in the storage position. This embodiment utilizes the shaft 32 illustrated in FIG. 7 having a first non-engaging portion 44a and a second non-engaging portion 44b. The first non-engaging portion 44a is positioned proximate the brake member 74 and the second non-engaging portion 44b is positioned proximate the shaft seal 92. The third engaging portion 42c is disposed intermediate the brake member 74 and the shaft seal 92. The third engaging portion 42c has an outer diameter that is larger than the inner diameter of the shaft seal 92 and the inner diameter of the brake member 74. Thus, while the third engaging portion 42c can be passed through the shaft seal 92 and/or the brake member 74 during the operational stroke of the syringe, the frictional force must be overcome by the user. If the prefilled retractable safety syringe 200 is merely subjected to reduced atmospheric pressures, such as during an air shipment, an expansion of an air bubble in the liquid chamber 34 (FIG. 2) will not impart sufficient force upon the piston 26 to overcome the frictional force between the third engaging portion 42c and the brake member 74. Therefore, in the storage position, the plunger assembly 37 is generally "locked" into place and unwanted stopper movement is reduced, if not eliminated. By locking the plunger assembly 37 in place, the chances of a sterility failure of the prefilled syringe during shipment is greatly reduced.

With reference now to the operation of the retractable safety syringe illustrated in FIG. 2, during an operational stroke, the vacuum chamber 12 is enlarged upon movement of the plunger assembly 37 toward the distal portion 20 such that the internal volume of the vacuum chamber 12 is increased. Movement of the plunger assembly 37 out of the storage position (FIG. 2) and into a working position (see e.g., FIGS. 16B and 17B) seals the vacuum chamber 12 and a vacuum created within the vacuum chamber 12 may exert a retraction force upon the plunger assembly 37. As will be understood by one of skill, the retraction force may be exerted upon the shaft 32 indirectly via exertion upon the proximal surface of the piston 26. The retraction force may vary as the plunger assembly 37 moves toward the distal portion 20 or toward the proximal portion 24. Thus, the retraction force may increase or decrease, respectively. The retraction force may be exerted on the plunger assembly 37 directed from the distal portion 20 toward the proximal portion 24. The retraction force may be caused due to a vacuum pressure in the vacuum chamber 12.

When the retractable safety syringe 10 is in the filling position, the needle 14 may be inserted into a medication container containing fluidic medication. The medical professional or user may slip his or her fingers underneath the thumb platform 30 and pull the thumb platform 30 away from the syringe body 16. Note that even though the vacuum chamber 12 is exerting a vacuum force on the piston 26 when the retractable safety syringe 10 is in the filling position, the force exerted by the brake member 74 on the shaft 32 exceeds the vacuum force. As the plunger assembly 37 is traversed toward the retracted position, the fluid within the medication container is transferred into the fluid chamber 34 via the needle 14. When the appropriate amount of fluidic medication is filled in the variable fluid chamber 34, the user stops traversing the thumb platform 30 away from the syringe body 16. The user or medical professional removes the needle 14 from the medication container. A small amount of air may be trapped within the variable fluid chamber 34. To remove the trapped air, the user or medical professional may invert the retractable safety syringe 10 such that the needle 14 is pointed upwardly. The user or medical professional taps the outside surface of the syringe body 16 to urge the trapped air within the fluid chamber 34 toward the needle tip. The medical professional or user may place his or her first and second fingers underneath the finger platforms 31 and place his or her thumb on the thumb platform 30. When the thumb platform 30 is depressed to remove the trapped air within the fluid chamber 34, a retraction force is created by the vacuum chamber 12 when the plunger assembly 37 is traversed toward the engaged position to remove trapped air within the variable fluid chamber 34. The force exerted by the brake member 74 on the shaft 32 exceeds the retraction force, thereby allowing the medical professional or user to remove their thumb from the thumb platform 30, if necessary.

At this moment, the retractable safety syringe 10 has been prepared to inject the fluidic medication into a patient. In one embodiment, the retractable safety syringe 10 may be prefilled and delivered to the user or medical professional with a predetermined amount of fluidic medication. In any event, the needle 14 is inserted into the patient and the plunger assembly 37 is traversed from the retracted position to the engaged position. The user or medical professional traverses the plunger assembly 37 from the retracted position to the engaged position by placing his or her first and second fingers under the finger platforms 31 and his or her thumb on the thumb platform 30. As the vacuum chamber 12 is enlarged it produces a retraction force which urges the plunger assembly toward the retracted position. When the plunger assembly 37 is traversed to the engaged position, the piston 26 may engage the needle holder 18 and needle 14. As the plunger assembly 37 is traversed to the engaged position, the ram 33 contacts the brake member 74 and pushes the brake member 74 out of the cover 72 and within the lower step 80 (see FIG. 3). With the brake member 74 pushed from the cover 72, the brake member no longer applies a braking force to the shaft 32.

Once the piston 26 engages the needle holder 18 and needle 14, the user or medical professional may release pressure on the thumb platform 30 such that the retraction force is greater than the thumb pressure and the plunger assembly 37 is urged back toward the retracted position (see FIG. 6). The needle holder 18 and needle 14 are urged back into body 16 thereby covering the needle 14 and preventing accidental needle prickings and needle reuse. Also, the needle 14 may be canted toward one side of the syringe body 16. Canting the needle 14 toward one side of the syringe body 16 keeps the needle 14 from accidentally protruding through the distal end of the syringe body 16.

The piston 26 may be engageable to the needle holder 18 and needle 14 via any method known in the art. By way of example and not limitation, the piston 26 may be engageable to the needle holder 18 and needle 14 via the structure disclosed in U.S. Pat. No. 6,413,236, the entire content of which is expressly incorporated herein by reference. The piston 26 may be engageable to the needle holder 18 and needle 14 via the structure disclosed in concurrently filed application Ser. No. 12/842,885 entitled "MULTI-CHAMBERED RETRACTABLE SAFETY SYRINGE" and filed Jul. 23, 2010, the entire disclosure of which is expressly incorporated herein by reference.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

The invention claimed is:
1. A retractable safety syringe for preventing accidental needle pricking and needle reuse after completion of an injection stroke, the syringe comprising:
    a syringe body defining a proximal portion and a distal portion;
    a needle removeably engageable to the body distal portion;
    a piston disposed within the syringe body and biasable to the body proximal portion via a vacuum force when the piston is traversed toward the syringe body distal por- tion, the piston being traverseable between a retracted position and an engaged position;

a shaft attached to the piston and disposed within the body, at least one of the shaft and the syringe body including a seal, the shaft extending through the proximal portion of the body;

a vacuum chamber disposed within the syringe body, the vacuum chamber located intermediate the piston and the seal, the vacuum chamber configured to provide the vacuum force on the piston in a direction from the syringe body distal portion toward the syringe body proximal portion upon movement of the piston toward the syringe body distal portion responsive to the distal translation of the piston; and a fluid chamber disposed within the syringe body, the fluid chamber located distally from the piston, the fluid chamber having a distal end and a proximal end, the proximal end of the fluid chamber being sealed, the fluid chamber in fluid communication with the needle through the distal end of the fluid chamber and configured to be reduced in volume as the piston is traversed towards the engaged position, and wherein at least one of the shaft and the syringe body includes an engaging portion and a non-engaging portion, traversal of the shaft through the syringe body operative to traverse the piston within the syringe body between a storage position and working positions, the engaging portion proximate the seal and in sealing engagement with the seal in the working positions and the non-engaging portion proximate the seal and in a substantially non-sealing engagement with the seal in the storage position.

2. The retractable safety syringe of claim 1, wherein the needle is coupled to a needle holder, the needle holder removeably engageable to the body distal portion.

3. The retractable safety syringe of claim 1, wherein the seal is located in the proximal portion of the syringe body.

4. The retractable safety syringe of claim 1, wherein the seal is located on a proximal side of the vacuum chamber.

5. The retractable safety syringe of claim 1, wherein the shaft includes the engaging portion and the non-engaging portion, and wherein the engaging portion has a first outer diameter and the non-engaging portion has a second outer diameter, the first outer diameter greater than the second outer diameter.

6. The retractable safety syringe of claim 1, further including a brake member disposed in a first cavity of the syringe body, the brake member proximate the non-engaging portion and in a substantially non-frictional engagement with the non-engaging portion when the shaft is in the storage position, the brake member biased toward and frictionally engaged to the engaging portion for providing a braking force to maintain a position of the piston within the syringe body before completion of the injection stroke when the shaft is in the working positions, the brake member completely disengaged from the shaft after completion of the injection stroke by axially traversing the brake member into a second cavity so the vacuum force withdraws the needle into the syringe body to prevent accidental needle pricking and needle reuse.

7. The retractable safety syringe of claim 1, wherein the non-engaging portion is positioned intermediate the piston and the engaging portion.

8. The retractable safety syringe of claim 1, wherein the non-engaging portion is proximally offset from the piston in the storage position.

9. The retractable safety syringe of claim 1, wherein the fluid chamber has a storage position volume that is a function of a distance between the piston and the non-engaging portion in the storage position.

10. The retractable safety syringe of claim 1, wherein the piston is offset from the syringe body distal portion in the storage position.

11. A retractable safety syringe for preventing accidental needle pricking and needle reuse after completion of an injection stroke, the syringe comprising:

a syringe body defining a proximal portion and a distal portion;

a needle removeably engageable to the body distal portion;

a piston disposed within the syringe body and biasable to the body proximal portion via a vacuum force when the piston is traversed toward the syringe body distal portion, the piston being traverseable between a retracted position and an engaged position;

a shaft attached to the piston and disposed within the body, at least one of the shaft and the syringe body including a seal, the shaft extending through the proximal portion of the body;

a vacuum chamber disposed within the syringe body, the vacuum chamber located intermediate the piston and the seal, the vacuum chamber configured to provide the vacuum force on the piston in a direction from the syringe body distal portion toward the syringe body proximal portion upon movement of the piston toward the syringe body distal portion responsive to the distal translation of the piston; and a fluid chamber disposed within the syringe body, the fluid chamber located distally from the piston, the fluid chamber having a distal end and a proximal end, the proximal end of the fluid chamber being sealed, the fluid chamber in fluid communication with the needle through the distal end of the fluid chamber and configured to be reduced in volume as the piston is traversed towards the engaged position, and wherein at least one of the shaft and the syringe body includes an engaging portion, traversal of the shaft through the syringe body operative to traverse the piston within the syringe body between a storage position and working positions, the engaging portion offset from the seal in the storage position and in sealing engagement with the seal in the working positions, the engaging portion and seal sealing the vacuum chamber when the piston is in the working position, the vacuum chamber being substantially unsealed when the piston is in the storage position.

12. The retractable safety syringe of claim 11, wherein at least one of the shaft and the syringe body includes a non-engaging portion, the non-engaging portion proximate the seal and in a substantially non-sealing engagement with the seal in the storage position.

13. The retractable safety syringe of claim 12, wherein the non-engaging portion is positioned intermediate the piston and the engaging portion.

14. The retractable safety syringe of claim 12, wherein the non-engaging portion is proximally offset from the piston in the storage position.

15. The retractable safety syringe of claim 11, wherein engagement of the engaging portion with the seal causes the vacuum force in the vacuum chamber.

16. A method of operating an automatically retracting syringe, the method comprising:
receiving a syringe comprising:
a syringe body defining a proximal portion and a distal portion;
a fluid chamber within the syringe body;
a needle removeably engageable to the body distal portion;
a shaft coupled to a piston, at least one of the shaft and the syringe body including a seal, the other of the shaft and the syringe body including at least one engaging portion and at least one non-engaging portion, the piston disposed in a storage position within the syringe body and substantially maintained in the storage position by the at least one engaging portion, the non-engaging portion positioned proximate the seal and in substantial non-sealing engagement;
a vacuum chamber within the syringe body configured to urge the piston toward a retracted position;
depressing a thumb platform to traverse the piston toward the distal portion of the syringe during an injection stroke;
inducing a biasing force on the piston via the vacuum chamber to urge the piston assembly back toward the retracted position;
engaging the piston to the needle upon completion of the injection stroke;
disengaging the needle from the syringe body;
removing thumb pressure on the thumb platform; and
traversing the needle into the syringe body under a biasing force.

17. The method of operating an automatically retracting syringe of claim 16, further including distally translating the non-engaging portion away from the seal when the thumb platform is depressed.

18. The method of operating an automatically retracting syringe of claim 16, wherein the fluid chamber is at least partially filled with fluidic medication when the syringe is received.

19. The method of operating an automatically retracting syringe of claim 16, wherein disengaging the needle from the syringe body includes disengaging a needle holder from the syringe body, the needle holder coupled to the needle.

* * * * *